United States Patent [19]

Laboureau et al.

[11] Patent Number: 4,899,745
[45] Date of Patent: Feb. 13, 1990

[54] SURGICAL CLIP FOR CUTANEOUS SUTURE AND TOOL FOR APPLYING IT

[76] Inventors: Jacques-Philippe Laboureau, 24 Fontaine Billenois; Georges Comte, 27 Bis Rue des Monts de Vigne, both of 21000 Dijon, France

[21] Appl. No.: 332,534

[22] Filed: Mar. 31, 1989

[30] Foreign Application Priority Data

Apr. 14, 1988 [FR] France .................................. 88 04945

[51] Int. Cl.⁴ ........................ A61B 17/08; F16B 15/00
[52] U.S. Cl. .................................... 606/142; 411/457; 606/151
[58] Field of Search .................. 128/334 C, 335, 337; 411/457

[56] References Cited

FOREIGN PATENT DOCUMENTS 0094752 10/1984 European Pat. Off. .............. 227/19
0180820 5/1986 European Pat. Off. .............. 227/19
0253629 1/1988 European Pat. Off. .............. 227/19

Primary Examiner—Edward M. Coven
Assistant Examiner—Gary Jackson
Attorney, Agent, or Firm—McAulay, Fisher, Nissen & Goldberg

[57] ABSTRACT

This invention relates to a surgical clip for cutaneous suture, wherein it successively comprises, starting from the centre of the clip and on each side of the plane of symmetry of the clip, a rectilinear branch, a first bend with concavity facing the skin into which the clip must be engaged, a second intermediate bend with convexity facing the skin and a third bend with concavity facing the skin, this third bend extending by an end leg terminating in the point of the clip and which is inclined by an angle of about 45° with respect to the general direction of extension of the clip. The invention also relates to a tool for applying said clip.

14 Claims, 3 Drawing Sheets

SURGICAL CLIP FOR CUTANEOUS SUTURE AND TOOL FOR APPLYING IT

FIELD OF THE INVENTION

The present invention relates to a surgical clip for cutaneous suture and to a tool for applying it.

BACKGROUND OF THE INVENTION

Surgical clips are already known, made of pre-shaped sheet metal which are placed one by one with the aid of a sort of tweezers and which present the drawbacks of not being very sharp, of being cumbersome and consequently of not being suitable for use in a stapler. On the other hand, one of their advantages is constituted by a stop on the point which limits penetration thereof.

Furthermore, other pre-shaped surgical clips are known, made of metal wire, which are used with a sterile, generally disposable stapler. Such clips, sharper and less cumbersome than the clips in pre-shaped sheet metal, close approximately in the form of a ring in the manner of a suture yarn knotted in conventional manner. Consequently, they present the drawback of exerting pressure only at the point of penetration of their point without taking into account the anisotropy constituted by the presence of the sides of a wound. However, a mode of suture employing yarn is known, practised in cosmetic surgery, called Blair-Donati suture, which is effected by disposing the fastening knot on one side only of the wound, therefore requiring that the yarn enters and leaves by the same side, which produces four traces of penetration of the yarn around the wound. This type of suture distributes the pressure exerted so that the deep layers of the skin receive a pressure which is equal to or greater than that of the surface layers. The normal tension of the skin does not move these deep layers apart and healing takes place both in depth and on the surface, with the result that, when the stitches are removed, the deep layers serve as hinge and the surface layers, in that case slightly in compression, continue to heal under better conditions.

It is an object of the present invention to overcome these drawbacks of known surgical clips by providing a clip whose shape is designed so as to limit the penetration of its points, thus avoiding forming a ring, and ensuring at the same time a better distribution of the pressure on the different cutaneous and sub-cutaneous layers between the points of the clip and its web.

SUMMARY OF THE INVENTION

To that end, this surgical clip for cutaneous suture constituted by a piece of wire made of a rigid but deformable material, particularly of metal, symmetrical with respect to a plane, terminated by two points and presenting, in the open state, a sinuous shape, is characterized in that it successively comprises, starting from the centre of the clip and on each side of the plane of symmetry of the clip, a rectilinear branch, a first bend with concavity facing the skin into which the clip must be engaged, a second intermediate bend with convexity facing the skin and a third bend with concavity facing the skin, this third bend extending by an end leg terminating in the point of the clip and which is inclined by an angle of about 45° with respect to the general direction of extension of the clip. The invention also relates to a tool for applying such a surgical clip for cutaneous suture, comprising an anvil member on which is applied the central part of the clip and a mobile presser coming into contact with the lateral parts of the clip in order to bend them around the anvil, characterized in that it comprises, in its face turned towards the anvil, a recess whose width is greater than that of the anvil member and defining, on either side, bearing faces coming into contact, in the first place, in the course of the movement of deformation of the clip around the anvil member causing closure thereof, with the outer third bends of the clip.

BRIEF DESCRIPTION OF THE DRAWINGS

The invention will be more readily understood on reading the following description with reference to the accompanying drawings, in which.

DETAILED DESCRIPTION OF THE DRAWINGS

Figure 1:
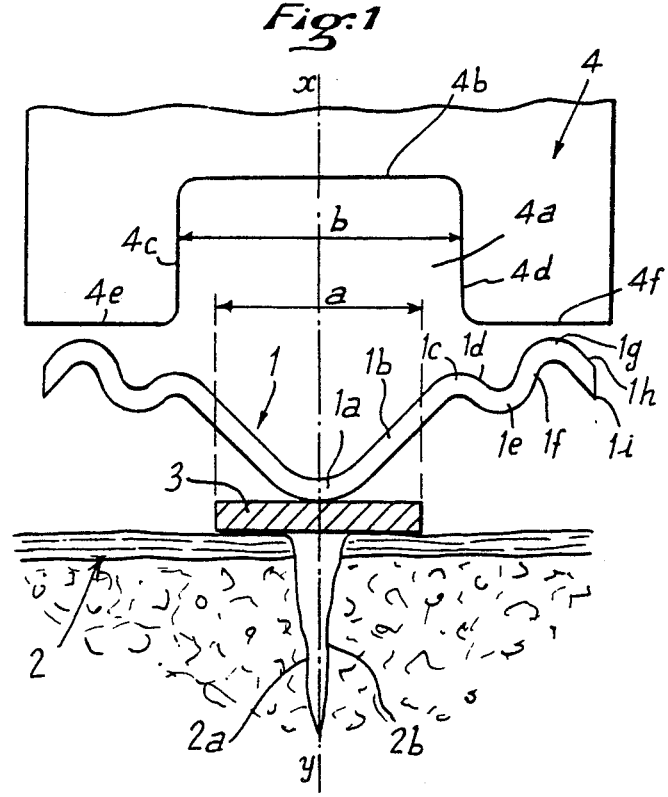
FIG. 1 is a view in elevation of a surgical clip according to the invention, in its state before being placed in position to suture a wound.

Referring now to the drawings, the surgical clip for cutaneous suture according to the invention is shown in FIG. 1 in the open, i.e. undeformed, state, and in that case it presents the general shape of an upwardly open, obtuse-angled V. This clip 1 which is symmetrical with respect to a vertical plane xy, is intended for suturing a wound in the skin 2 defined by two sides 2a, 2b. To ensure such a suture, the clip 1 is closed, using a tool comprising a horizontal anvil member 3, of rectangular vertical cross section, located beneath the chip and in contact with the surface of the skin, the clip 1 being in abutment on the anvil member 3 by its rounded central web 1a, with downwardly facing convexity, and a presser 4 located above the clip 1, the anvil member 3 and the presser 4 each being symmetrical with respect to the vertical plane xy.

As may be seen in FIG. 1, the surgical clip 1 presents on each side, starting from its rounded central web 1a, a rectilinear branch 1b inclined upwardly, a bend 1c with concavity facing downwardly, of an angle slightly larger than 90°, a short leg 1d inclined downwardly, a second bend 1e with concavity facing upwardly, of angle slightly smaller than 90°, an intermediate leg 1f, a third bend 1g with concavity facing downwardly, of angle slightly less than 90°, and an end leg 1h terminating in a bevelled face constituting a point 1i. This end leg 1h forms with the horizontal, i.e. with the general direction of extension of the clip, an angle substantially equal to 45°.

The anvil member 3 which is located beneath clip 1, has a width a which determines, in combination with the upper presser 4, the overall width of the surgical clip 1 once the latter is closed. The presser 4 presents, in the central part of its lower face, a rectangular recess 4a defined by an upper horizontal bottom 4b and two lateral, vertical sides 4c and 4d. The width b of the recess 4a, i.e. the distance between the lateral, vertical sides 4c, 4d, is slightly larger than the width a of the anvil member 3.

Figure 2:
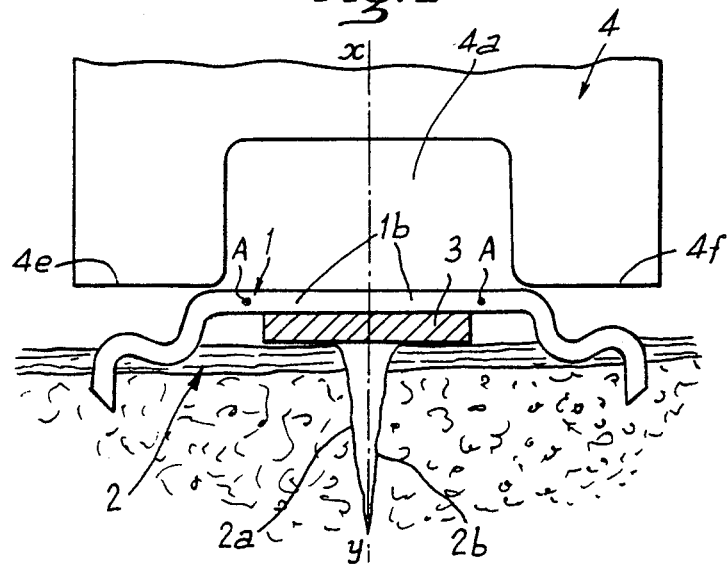
FIGS. 2 and 3 are similar views of the clip, respectively deformed in intermediate position flat, and in final position closed.
Figure 3:
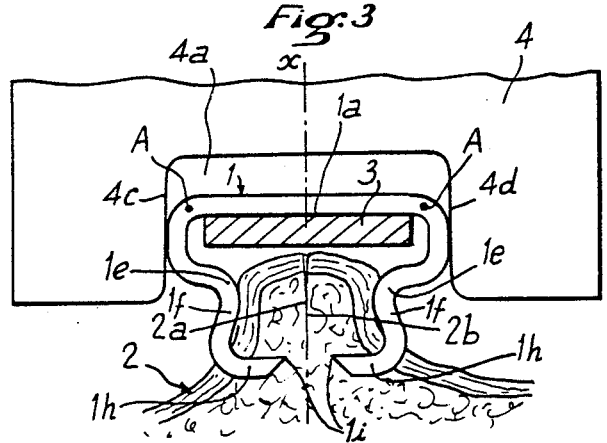

In order to position the clip 1 for the purpose of suturing a wound located therebeneath, the presser 4 is lowered, the anvil member 3 remaining fixed and holding the curved central web 1a of the clip 1. In the course of the descending movement of the presser 4, the latter comes into contact, by its lower faces 4e, 4f, with the bends 1g of the clip 1 and, from that moment, the presser 4 deforms the clip 1 which is progressively flattened to arrive in the intermediate position illustrated in FIG. 2 in which the clip is horizontal. When the downward movement of the presser 4 is continued, the legs 1b of the clip 1 are then retained against the upper face of the anvil member 3, over the major part of their length, and their end parts, by which they are joined to the bends 1c, are then deformed downwardly by pivoting about points A. These end parts are bent downwardly through 90° when the clip is closed (FIG. 3) and in this position, they extend vertically at a certain distance from the vertical sides of the anvil member 3. Due to this movement of pivoting of the end parts of the legs 1b about points A, the rest of the clip, constituted by parts 1c–1i, also pivots about points A in the direction of the vertical plane of symmetry xy, to the position of closure illustrated in FIG. 3. In this position of closure, the two end legs 1h, terminating in points 1i, extend substantially horizontally towards each other, being anchored in the two sides 2a, 2b of the wound. Furthermore, the leg 1f and the bend 1e constitute, on each side, a heel limiting penetration of the point 1h, 1i, on the one hand, and transmitting, on the other hand, a mechanical pressure distributed between point 1h, 1i and the web 1a of the clip which may present any shape. When the clip is closed, the two legs 1f converge slightly towards each other, upwardly, and they contribute efficiently to the tightening of the sides 2a, 2b of the wound 4. Furthermore, from the foregoing description, it may be seen that each side of the wound 2a, 2b is held at two points, namely at a first, deep point, at the location of point 1h, 1i, and, on the other hand, at a relatively superficial point at the location of the heel constituted by the leg 1f and the bend 1e. This ensures encounter with its counter-lateral homologue, as in the case of a so-called Blair-Donati stitch. Furthermore, due to the sinuous shape of the clip, the latter cannot rotate on itself as is the case of clips which, once closed, are similar to a circle and which present the drawback that their possible rotation creates shears detrimental to ideal healing.

Figure 4:
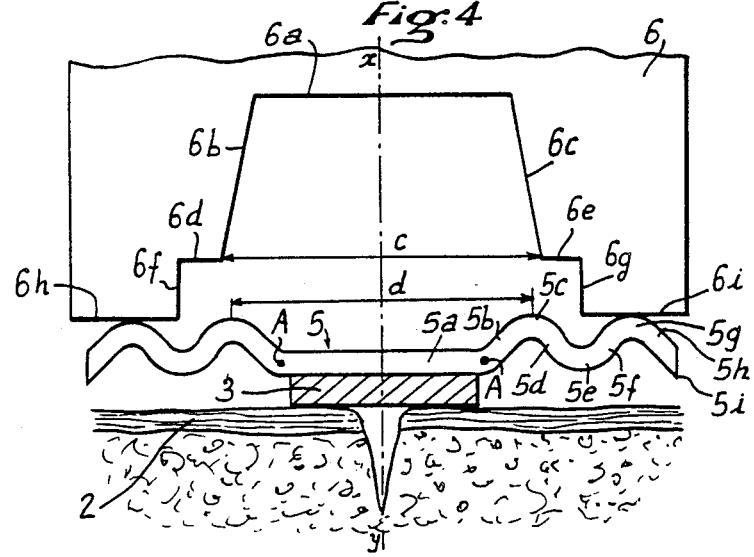
FIG. 4 is a view in elevation of a variant embodiment of the clip.
Figure 5:
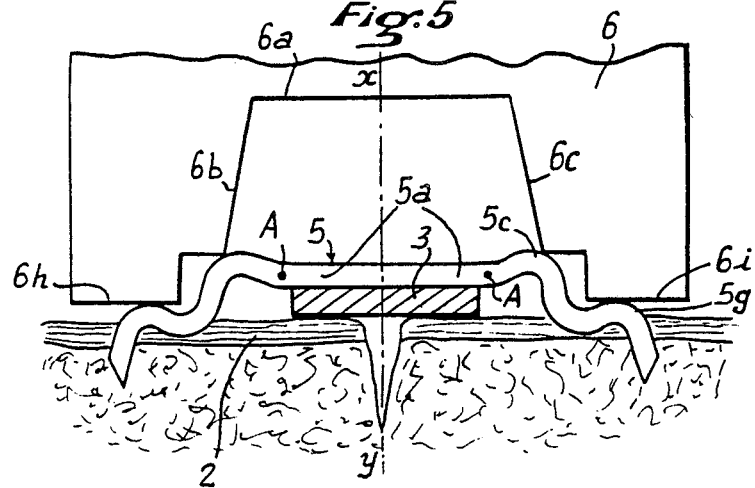
FIGS. 5, 6 and 7 are similar views illustrating the progressive deformation of the clip of FIG. 4 in the course of positioning thereof.
Figure 6:
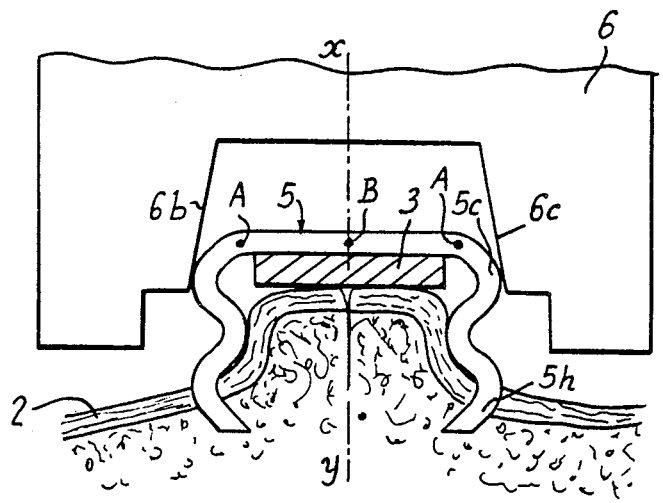
Figure 7:
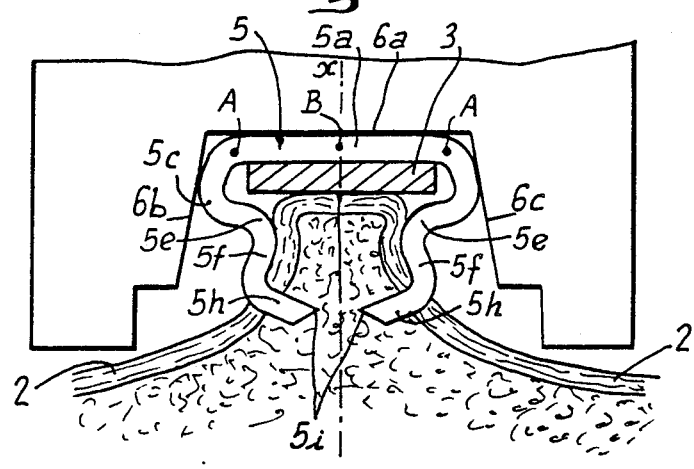

In the variant embodiment of the invention shown in FIG. 4, the surgical clip 5 is substantially flat in state of rest, being symmetrical with respect to the vertical plane xy. On each side of this plane and starting therefrom, the clip 5 successively comprises a horizontal rectilinear branch 5a extending above the anvil member 3, a short leg 5b inclined upwardly, a bend 5c with concavity facing downwardly, of an angle substantially equal to 90°, a short leg 5d, a bend 5e with concavity facing upwardly, of an angle substantially equal to 90°, a short leg 5f inclined upwardly, a bend 5g with concavity facing downwardly, of an angle substantially equal to 90°, and an end leg 5h inclined downwardly, by an angle of about 45° with respect to the horizontal, and terminated in a substantially vertical, bevelled face, defining a point 5i. With the anvil 3 there cooperates a mobile presser 6 presenting, in its lower face, a stepped recess comprising an upper, inner part of trapezoidal vertical section and a lower or outer part of rectangular vertical section. The upper part of trapezoidal vertical section is defined by an upper horizontal bottom 6a and two inclined lateral faces 6b, 6c which respectively join horizontal faces 6d, 6e, extending outwardly, constituting the upper faces of the lower rectangular recess and which are themselves extended downwardly by vertical lateral faces 6f, 6g opening out in the lower face of the cutter 6. This lower face is consequently limited to two lateral parts 6h, 6i extending horizontally. The width c of the lower large base of the upper trapezoidal part of the recess, i.e. the distance between the edges of join between the inclined lateral faces 6b, 6c and the horizontal faces 6d, 6e, is chosen to be equal to or slightly greater than the distance d between the apices of the two bends 5c of the clip 5. Furthermore, the two horizontal lower faces 6h, 6i of the presser 6 are spaced apart from each other by a distance such that, during the movement of the presser 6 towards the anvil member 3, they come into contact with the apices of the outer bends 5g of the clip 5 flat on the anvil member 3. From the moment when such contact is established, the lateral parts of the clip 3 are bent around the points A of join between legs 5a and 5b. The horizontal legs 5a remain applied on the upper face of the anvil member 3 whilst the rest of the clip is bent. At a certain moment of the continuing movement of descent of the presser 6, the intermediate horizontal faces 6d, 6e come into contact with the inner bends 5c, as shown in FIG. 5. From that moment, the deformation of the clip is ensured by the efforts exerted downwardly by the intermediate horizontal faces 6d, 6e on the inner bends 5c. These bends are thus progressively bent in the direction of the vertical plane xy, enveloping the anvil member 3, and, at a certain moment, as shown in FIG. 6, these partially bent bends 5c engage in the lower large base of the trapezoidal part of the recess, in that case being in contact with the inclined lateral faces 6b, 6c thereof. From that moment, deformation of the clip is ensured by these inclined faces 6b, 6c which, during the movement of descent of the presser 6, progressively push the two bends 5c in the direction of the anvil member 8. Such deformation leading to the closure of the clip continues until the upper bottom 6a of the trapezoidal recess comes into contact with the horizontal legs 5a of the clip 5 in abutment on the anvil member 3. At that moment, the clip 5 is totally closed as shown in FIG. 7. In this position of closure, the end legs 5h are slightly inclined downwardly, one towards the other and towards the vertical plane of symmetry xy, their points 5i being close to each other, on either side of the plane xy. There again, the legs 5f and the bends 5e constitute heels similar to heels 1f, 1e of the clip 1 described hereinabove and performing the same role.

With the clip 5 which has just been described and whose closure is finally ensured by the contact of the clip with the inner faces 6b, 6c of the trapezoidal upper part of the presser 6, it is necessary to provide a considerable stroke of this presser 6 for a given stroke of the points 5i of the clip. Furthermore, this makes it possible to use an adjustable stapler, avoiding the use of several sizes of clips. The clip may thus be closed more or less by adjusting the stroke of the stapler accordingly.

It will be noted that, during positioning of the clip 5, its points 5i pivot about points A, describing an engaging path which tends to descend the web of the clip, constituted by the legs 5a, on the suture. On the other hand, upon opening of the clip, the centre of rotation is the point B located in the middle of legs 5a, which allows a neutral path of the points 5*i*, thus avoiding traumatism upon extraction.

The different forms of the clip flat and the clip closed are subjected to another servitude which is that of allowing stacking of the clips, with the result that the pitch of the clips does not exceed 1.4 times the diameter of the wire constituting them, in order to present clip loaders allowing the maximum quantity in the minimum volume. V-shaped clips 1 or flat clips 5 as described hereinabove are particularly well adapted to such an imbrication.

What is claimed is:

1. A surgical clip for cutaneous suture constituted by a piece of wire made of a rigid but deformable material, particularly of metal, symmetrical with respect to a plane, terminated by two points and presenting, in the open state, a sinuous shape,
wherein it successively comprises, starting from the centre of the clip and on each side of the plane of symmetry of the clip, a rectilinear branch, a first bend with concavity facing the skin into which the clip must be engaged, a second intermediate bend with convexity facing the skin and a third bend with concavity facing the skin, this third bend extending by an end leg terminating in the point of the clip and which is inclined by an angle of about 45° with respect to the general direction of extension of the clip.

2. The surgical clip of claim 1, wherein the clip has the general form of an obtuse-angled V and it comprises a rounded central web, at the location of the apex of the V, which joins the two rectilinear branches.

3. A tool for applying the surgical clip for cutaneous suture of claim 2, comprising an anvil member on which is applied the central part of the clip and mobile presser coming into contact with the lateral parts of the clip in order to bend them around the anvil, comprising in its face turned towards the anvil member, a recess whose width is greater than that of the anvil member and defining, on either side, bearing faces coming into contact, in the first place, in the course of the movement of deformation of the clip around the anvil member causing closure thereof, with the outer third bends of the clip.

4. The surgical clip of claim 1, wherein the clip has a flat shape in the open state and its two rectilinear central branches are coaxial.

5. A tool for applying the surgical clip for cutaneous suture according to claim 4 comprising in its face turned towards the anvil member, a recess whose width is greater than that of the anvil member and defining, on either side, bearing faces coming into contact, in the first place, in the course of the movement of deformation of the clip around the anvil member causing closure thereof, with the outer third bends of the clip.

6. A tool for applying the surgical clip for cutaneous suture of claim 1, comprising an anvil member on which is applied the central part of the clip and a mobile presser coming into contact with the lateral parts of the clip in order to bend them around the anvil,
wherein it comprises, in its face turned towards the anvil member, a recess whose width is greater than that of the anvil member and defining, on either side, bearing faces coming into contact, in the first place, in the course of the movement of deformation of the clip around the anvil member causing closure thereof, with the outer third bends of the clip.

7. The tool of claim 6, wherein the recess of the presser has a rectangular shape, it is defined by a bottom and two lateral sides, the distance between these lateral sides being greater than the width of the anvil member.

8. The tool of claim 6, wherein the recess of the presser comprises an upper or inner part of trapezoidal vertical section which is defined by a upper horizontal bottom and two inclined lateral faces, and a lower or outer part of rectangular vertical section which comprises two outwardly extending horizontal faces, constituting the upper faces of the lower rectangular recess and which are themselves extended downwardly by vertical lateral faces opening out in the lower face of the presser which is consequently limited to two horizontally extending, lateral parts.

9. The tool of claim 8, wherein the two horizontal lower faces of the presser are spaced apart from each other by a distance such that, during the movement of the presser towards the anvil member, they come into contact with the apices of the outer third bends of the clip flat on the anvil member.

10. The tool of claim 9, wherein the width of the large lower base of the upper trapezoidal part of the recess, i.e., the distance between the edges of join between the inclined lateral faces and the horizontal faces, is equal to or slightly larger than the distance between the apices of the two first blends of the clip.

11. The tool of claim 9, wherein it allows, by the width of the presser and the trapezoidal shape of its upper part, an adjustment of the closure of the clip depending on the nature of the skin to be sutured, avoiding the use of clips of different sizes.

12. The tool of claim 8, wherein the width of the large lower base of the upper trapezoidal part of the recess, i.e. the distance between the edges of join between the inclined lateral faces and the horizontal faces, is equal to or slightly larger than the distance between the apices of the two first bends of the clip.

13. The tool of claim 12, wherein it allows, by the width of the presser and the trapezoidal shape of its upper part, an adjustment of the closure of the clip depending on the nature of the skin to be sutured, avoiding the use of clips of different sizes.

14. The tool of claim 8, wherein it allows, by the width of the presser and the trapezoidal shape of its upper part, an adjustment of the closure of the clip depending on the nature of the skin to be sutured, avoiding the use of clips of different sizes.

* * * * *